United States Patent [19]

Landolfi

[11] Patent Number: 5,349,053
[45] Date of Patent: Sep. 20, 1994

[54] CHIMERIC LIGAND/IMMUNOGLOBULIN MOLECULES AND THEIR USES

[75] Inventor: Nicholas F. Landolfi, Mountain View, Calif.

[73] Assignee: Protein Design Labs, Inc., Mountain View, Calif.

[21] Appl. No.: 76,263

[22] Filed: Jun. 10, 1993

Related U.S. Application Data

[63] Continuation of Ser. No. 532,267, Jun. 1, 1990, abandoned.

[51] Int. Cl.[5] .................... C07K 13/00; A61K 39/00; A61K 37/02
[52] U.S. Cl. .................... 530/351; 530/387.1; 530/387.3; 530/387.9; 530/388.1; 530/388.25; 530/389.1; 530/391.1; 530/391.7; 530/391.9; 424/85.2; 424/134.1; 930/141
[58] Field of Search .............. 530/351, 387.1, 387.3, 530/387.9, 388.1, 388.25, 389.1, 389.3, 391.1, 391.7, 391.9; 424/85.2, 85.8, 85.9; 930/141

[56] References Cited

FOREIGN PATENT DOCUMENTS

| | | |
|---|---|---|
| 305967 | 3/1989 | European Pat. Off. . |
| 0314317 | 3/1989 | European Pat. Off. . |
| 367166 | 5/1990 | European Pat. Off. . |
| 0396387 | 11/1990 | European Pat. Off. . |
| WO86/01533 | 3/1986 | PCT Int'l Appl. . |
| WO89/02922 | 6/1989 | PCT Int'l Appl. . |
| 9101004 | 1/1991 | PCT Int'l Appl. . |

OTHER PUBLICATIONS

Fell et al, *J Immunol.* 146, 1991, pp. 2446–2452.
Ikeyama, *Mol. Immunol* 24(10) 1987, pp. 1039–1046.
Wildner et al, *Mol Immunol.* 26(1) 1989, pp. 33–40.
Gross et al, *PNAS* 86, 1989, pp. 10024–10028.
Morrison et al, CA vol 116(3), 1991, #19660a.
Ashenozi et al, CA vol 116(3), 1991, #19532k.
Morrison, S. L. *Science*, 229, 1202–1207 (1985).
Neuberger, M. S. et al., *Nature*, 312, 604–608 (1984).
Schnee, J. M. et al., *Proc. Natl. Acad. Sci. U.S.A.*, 84, 6904–6908 (1987).
Pastan, I. et al. *Cell*, 47, 641–648 (1986).
Chaudhary, V. K. et al. *Nature*, 339, 394–397 (1989).
Morrison, S. L. et al., *Proc. Natl. Acad. Sci. U.S.A.*, 81, 6851–6855 (1984).
Boullianne G. L. et al., *Nature*, 312, 643–646 (1984).
Jones, P. T. et al., *Nature*, 321, 522–525 (1986).
Reichmann, L. et al., *Nature*, 332, 323–327 (1988).
Queen, C. et al., *Proc. Natl. Acad. Sci., U.S.A.*, 86, 10029–10033 (1989).
Capon, D. J. et al., *Nature* 337, 525–530 (1989).
Traunecker, A. et al., *Nature*, 339, 68–70 (1989).
Byrn, R. A. et al., *Nature*, 344, 667–670 (1990).
Rodwell, J. D., *Nature*, 342, 99–100 (1989).

*Primary Examiner*—Garnette D. Draper
*Attorney, Agent, or Firm*—Townsend and Townsend Khourie and Crew

[57] ABSTRACT

Chimeric molecules having a ligand component linked to an immunoglobulin constant region component are provided for various diagnostic, therapeutic and other uses. These immunoligands can exhibit the high degree of specificity associated with the ligand, yet retain various effector functions characteristic of immunoglobulin heavy chains.

12 Claims, 4 Drawing Sheets

sure and 5,349,053

CHIMERIC LIGAND/IMMUNOGLOBULIN MOLECULES AND THEIR USES

This is a continuation of application Ser. No. 07/532,267, filed Jun. 1, 1990, now abandoned.

BACKGROUND OF THE INVENTION

The present invention relates generally to the production of chimeric molecules. In particular, it relates to the production of chimeric molecules (immunoligands) comprising at least a portion of a ligand molecule linked to an immunoglobulin constant region.

The basic immunoglobulin structural unit is known to comprise a tetramer. Each tetramer is composed of two identical pairs of polypeptide chains, each pair having one "light" (about 25 kD) and one "heavy" chain (about 50–70 kD). The N-terminal portion of each chain defines a variable region of about 100 to 110 or more amino acids primarily responsible for antigen recognition. The C-terminal portion of each chain defines a constant region primarily responsible for effector function.

Light chains are classified as either kappa or lambda. Heavy chains are classified as gamma, mu, alpha, delta, or epsilon, which in turn define the immunoglobulin classes, IgG, IgM, IgA, IgD and IgE, respectively.

Within the light and heavy chain, units made up of about 110 amino acids form discrete domains. Each domain is held together by a single internal disulfide bond. The heavy chain typically contains 4 such domains, while the light chain contains 2. The first N-terminal domain of the heavy chain, $V_H$, interacts with the N-terminal domain of the light chain, $V_L$, to produce the binding region of the antibody. Moving towards the C-terminus, the next three domains of the heavy chain are designated $C_H1$, $C_H2$, and $C_H3$, respectively. The mu and epsilon heavy chains contain an additional domain, $C_H4$.

Most heavy chains have a hinge region between the $C_H1$ and $C_H2$ domains consisting of a small number of amino acids. The hinge is flexible and allows the binding region to move freely relative to the rest of the molecule. At the hinge region are the disulfide bridges which hold the two dimers together, creating the tetramer structural unit.

The hinge region is the point on the molecule most susceptible to the action of protease. Treatment with the protease papain splits the molecule into three fragments, two of which are designated $F_{ab}$ fragments, and the other, the $F_c$ fragment. The $F_{ab}$ fragments each consist of an antigen binding domain and a $C_H1$ domain. Further proteolytic digestion of the $F_{ab}$ fragments releases the $F_v$ fragment, which consists only of the variable region.

The $F_c$ fragment, which consists of the $C_H2$ and $C_H3$ domains, is the portion of the immunoglobulin molecule that mediates effector functions. Depending upon the heavy chain in the immunoglobulin, a variety of effector functions are present. These include complement fixation, mediation of antibody dependent cell toxicity, stimulation of B cells, transport across the placenta, and longer serum half-life (see, generally, Hood, et al. *Immunology* (1984, 2d ed.), which is incorporated herein by reference).

Recent advances in molecular biology have provided methods for genetically engineering immunoglobulin molecules. While significant success has been made in changing the specificity of immunoglobulins (e.g., by replacing the complementarity determining regions), the majority of efforts seem to have focused on the constant region. For instance, the constant region has been totally or partly replaced with cytotoxic molecules to produce immunotoxins. Enzymes and other molecules have been attached to $F_v$ regions to produce chimeric molecules having novel properties. In addition, portions of immunoglobulins from different species have been combined to produce novel molecules. Recently, additional chimeric molecules have also been constructed composed of a T cell surface receptor glycoprotein (CD4) in the immunoglobulin gene superfamily fused to an immunoglobulin constant region.

While these modifications have proved successful in broadening the potential use of immunoglobulins, some significant limitations remain. For instance, although mammals create an immunoglobulin array with an astounding range of reactivity, producing an immunoglobulin with a precisely predetermined specificity is essentially always a matter of chance. Typically, a large number of candidates must be laboriously screened before a possibly suitable immunoglobulin is identified. In many cases, an immunoglobulin having the desired specificity and affinity is never located, particularly if immunogenicity is also an important consideration. Problems of cross-reactivity and relatively weak binding affinity can especially hinder the usefulness of immunoglobulins in therapeutic applications.

Thus, there exists a need for increasing the specificity and improving binding affinity of immunoglobulins beyond the immunoglobulin gene superfamily, while retaining their other useful characteristics. The molecules should be capable of production in an economical manner, preferably suitable for pharmaceutical application. The present invention fulfills these and other needs.

SUMMARY OF THE INVENTION

The present invention provides immunoligands having a ligand component linked to an immunoglobulin constant region component, wherein the ligand component is capable of binding to a cell surface receptor and the immunoglobulin component is capable of mediating normal effector functions. The constant region component is preferably derived from an immunoglobulin heavy chain constant region, more preferably a human IgG1 heavy chain, such as a $C_H1$ domain, hinge region, a $C_H2$ domain, and/or a $C_H3$ domain.

The constant region component preferably retains its effector function. For instance, it may be capable of fixing complement or mediating antibody dependent cell cytotoxicity. The ligand component of the immunoligand can be derived from any ligand molecule (such as interleukin-2) or portion thereof capable of binding to a desired receptor. The ligand component is typically linked to the constant region component by a peptide bond.

In preferred embodiments, the immunoligand comprises a growth factor amino acid sequence capable of binding to a cell surface receptor, which moiety is conjugated to at least one domain of an immunoglobulin heavy chain constant region. Preferably, the heavy chain constant region is a human IgG1 heavy chain constant region. For example, an immunoligand may comprise interleukin-2 linked to a human IgG1 heavy chain constant region, which is useful in the treatment of various B and T cell related disorders.

The present invention also provides recombinant nucleic acid constructs encoding immunoligands and cells transformed with the nucleic acids. Also provided are methods for preparing immunoligands comprising transforming a host cell with such a recombinant construct and recovering the immunoligand from a culture of the host cell. A preferred host cell is a murine non-secreting myeloma cell line, which is capable of expressing large quantities of immunoligands.

A pharmaceutical composition comprising a suitable carrier and one or more immunoligands is also provided. These compositions are useful in methods for treating T cell mediated disorders in human patients, the methods comprising administering to the patient a therapeutically effective dose of such immunoligands.

BRIEF DESCRIPTION OF THE DRAWINGS

FIG. 1. Schematic diagram of pIL-2/IgG1 expression vector. This vector was constructed by inserting a slightly altered form of the human IL-2 gene into a modified form of the expression vector PVγ1 (Queen et al., *Proc. Natl. Acad. Sci.* 86:10029-34 (1989)) in which the XbaI site had been changed to a Sal1 site. The IL-2 gene employed differed from the natural sequence of human IL-2 (Taniguchi et al., *Nature* 302:305-310 (1983)) in that it encoded an alanine rather than a cysteine at position 125. The IL-2 gene had also been modified at the 3' end by the addition of a single codon for serine followed by a splice donor site to allow the 3' terminus of IL-2 to be spliced to the 5' end of CH1. The splice donor site and the next twenty bases of the intron were identical to that found at the end of the murine $J_{H}2$ segment (Sakano et al., *Nature* 286:675-683 (1980)). A 235 base pair intron separated the IL-2 and IgG1 genes. A Sal I site was also added to each end of the fragment to facilitate insertion into the vector. The arrow indicates the direction of transcription from the Ig kappa chain promoter; $E_H$ indicates the Ig heavy chain enhancer.

FIG. 2A-2C Biochemical analysis of the 87.20.12 transfectant. a) Immunoprecipitation of the supernatant (lanes 1-4) and cell lysate (lanes 5-8) from the 35S-labeled 87.20.12 cells. Lanes 1 and 5 were incubated with rabbit IgG agarose, lanes 2 and 6, goat anti-human IgG agarose, lanes 3 and 7, rabbit anti-human IL-2 agarose, and lanes 4 and 8, protein A agarose. b) $^{35}$S-labeled 87.20.12 lysate was cleared with rabbit IgG agarose (lane 1) or goat anti-human IgG agarose (lane 2), prior to immunoprecipitation with rabbit anti-IL-2 agarose (both lanes). c) 87.20.12 labelled supernatant was incubated with goat anti-human IgG agarose and the immunoprecipitate was electrophoresed under non-reducing (lane 1) or reducing (lane 2) conditions. The positions of molecular weight markers (in kilodatons) are indicated on the left of each panel.

FIG. 3. Cytofluorometric detection of the binding of IL-2/IgG1 to cell lines which express the IL-2 receptor. Profiles of the indicated cells incubated with: . . . , an irrelevant antibody; . . . , IL-2/IgG1;—humanized anti-Tac for HuT-102B, JURKAT and CEM, or PC 61 5.3 for CTLL, prior to incubation with the appropriate FITC-conjugated reagent (goat anti-human or goat anti-mouse). Histograms indicate the cell number versus the log of fluorescence intensity.

FIG. 4A-4B Functional analysis of the IL-2/IgG1 molecule. a) Varying concentrations of human recombinant IL-2 (●) or IL-2/IgG1 (○) were assayed for the ability to stimulate the proliferation of CTLL cells, as measured by the incorporation of $^3$H-thymidine (Robb et al., *J. Exp. Med.* 160:1126-1146 (1984). b) Varying concentration of the murine anti-Tac monoclonal antibody (●) or IL-2/IgG1 (○) were assayed for the ability to mediate complement dependent lysis of $^{51}$Cr-labeled HuT-102B cells.

DESCRIPTION OF THE PREFERRED EMBODIMENTS

The present invention provides chimeric molecules that comprise a portion of a ligand molecule linked to the constant region of an immunoglobulin molecule. The chimeric molecules of the present invention are referred to as immunoligands.

An immunoligand is a modified immunoglobulin in which a ligand component replaces all, or substantially all, of the variable region of the immunoglobulin. Thus, the ligand component determines the binding specificity of the molecule. A ligand is defined here as a synthetic or naturally-occurring peptide or protein molecule, not in the immunoglobulin superfamily (see, Hunkapiller and Hood, *Nature* 323:15 (1986), which is incorporated herein by reference), that bears one or more determinant sites allowing it to be recognized by a receptor molecule on a cell surface. If desired, the ligand may be modified in a variety of ways to provide an immunoligand with a predefined set of properties.

Despite conjugation to the ligand component, the normal effector function of the immunoglobulin constant region component may be retained. Thus, the immunoligand will preferably have most or all of the physiological properties associated with the constant region of the particular immunoglobulin class used. For example, depending upon the heavy chain used, the immunoligand may be capable of fixing complement, mediating antibody dependent cell toxicity, stimulating B cells, or traversing blood vessel walls and entering the interstitial spaces.

The constant region component of the present invention typically comprises one or more of the $C_H1$, $C_H2$, and $C_H3$ domains and the hinge region. As defined here, the constant region component may also comprise a portion of the variable region of the particular immunoglobulin chain, usually less than about 10 amino acids.

As used herein, the term "receptor" refers to a naturally-occurring cell surface molecule which recognizes a corresponding naturally-occurring ligand by the spatial or polar organization of the ligand's determinant site(s). The specific interaction of the receptor with a ligand determinant site usually involves the molecular complementarity typical of enzyme-substrate or antibody-antigen interactions. These interactions include noncovalent bonding such as ionic bonds, hydrogen bonds, van der Waals forces, and nonpolar interactions (see generally, Stryer, *Biochemistry* (3rd ed. 1988)).

Virtually any naturally-occurring ligand, or portion thereof, capable of binding to a receptor may be used as the ligand component in the present invention. Preferred examples of naturally-occurring ligands include growth factors, lymphokines, peptide hormones, lectins and adhesion molecules. Synthetic compounds which mimic the specificity of the naturally occurring compounds can also be used.

Hormones are one example of naturally occurring ligands. Highly characterized polypeptide hormones well known in the art include: oxytocin, insulin, thyroid stimulating hormone and various growth factors. Examples of growth factors include: erythropoietin, epidermal growth factor, granulocyte colony stimulating factor, granulocyte macrophage colony stimulating factor, fibroblast growth factor, transforming growth factors, platelet derived growth factor, insulin-like growth factor, osteogenic factors, nerve growth factors, lymphokines, megakaryocyte colony stimulating factor, macrophage colony stimulating factor, and human growth hormone. Other particularly suitable ligands include lymphokines, such as IL-1 through IL-8 (Paul, *Cell* 57:521–524 (1989), which is incorporated herein by reference) or their antagonists, e.g., IL-1 inhibitor (see, Hannum et al., *Nature* 343:336–340 (1990), which is incorporated herein by reference) and adhesion molecules, such as ICAM-1, ELAM-1, MAC-1 and LAF-3 (Stoolman, *Cell* 56:907–910 (1989), which is incorporated herein by reference).

Immunoligands have a number of advantages over native ligand molecules and immunoglobulins. A whole new range of cells can be targeted easily because the ligand component, not the immunoglobulin, determines specificity. In addition, the relatively short serum half-life of many small, therapeutically useful ligands can be increased by linking them to an immunoglobulin constant region.

In constructing the immunoligand, the immunoglobulin can be modified so that effector function is eliminated or reduced. Thus, the immunoglobulin component imparts serum stability without interfering with the activity of the ligand. The resulting molecule has enhanced therapeutic effectiveness, because a given dose is available in the serum of the patient for a longer period of time.

Immunoligands are valuable in a variety of other therapeutic applications. Such agents have particular therapeutic value if their binding specificity is unique to a neoplasia or other tissue characteristic of a disease state. Examples of such diseases include T or B cell lymphomas and leukemias and autoimmune diseases where the ligand can bind to the surface receptor (T cell receptor or surface Ig on the T or B cells respectively), and any form of cancer that overexpresses a receptor for a growth factor or cytokine. In the present embodiment, T cells expressing interleukin-2 receptors are targeted.

Depending upon the particular immunoglobulin constant region conjugated to the particular ligand, different effector functions may be obtained. For instance, if interleukin-2 is the ligand component, the targeted cells may be stimulated to proliferate, thus enhancing the immune response. Alternatively, the effector function may lead to the selective elimination of these cells if therapy for autoimmune diseases is desired. Elimination could be due to complement activation by the immunoligand. Alternatively the immunoligand may mediate antibody dependent cell cytotoxicity. Other applications include increasing the serum half life of the ligand molecule and/or mediating placental transfer.

To improve the elimination of the targeted cells, the immunoglobulin component can be further conjugated to a cytotoxic agent to create an immunotoxin. Methods for the production of various immunotoxins is well known in the art (see, generally, "Monoclonal Antibody-Toxin Conjugates: Aiming the Magic Bullet," Thorpe et al *Monoclonal Antibodies in Clinical Medicine*, Academic Press, pp. 168–190 (1982), which is incorporated herein by reference).

In addition to variation of the immunoglobulin, the ligand portion of the immunoligand may also be altered.

Typically, the ligand molecule will be altered so that only the portion of the molecule necessary for binding the receptor is left intact. Thus, the molecule binds the receptor but does not elicit the metabolic changes associated with binding. For instance, the interleukin-2 molecule can be altered to retain binding but lose the ability to stimulate T cell proliferation. This is accomplished by identifying amino acid residues responsible for T-cell activation, altering these residues (e.g., by replacement with different amino acids), and then selecting for the desired activities. The immunoligand can then be used as an antagonist to block the action of interleukin-2 and inhibit the immune response.

Immunoligands of the present invention can further find a wide variety of utilities in vitro. By way of example, they can be utilized for T cell typing, for isolating or labeling specific receptor bearing cells or fragments of the receptor, for vaccine preparation, or the like, all in accordance with well known procedures in the art.

For diagnostic purposes, the immunoligands may either be labeled or unlabeled. Unlabeled immunoligands can be used in combination with other labeled antibodies (second antibodies) that are reactive with the immunoglobulin portion of the molecule. Antibodies specific for human immunoglobulin constant regions are well known in the art (see, generally, Harlow and Lane, *Antibodies: A Laboratory Manual* (1988), which is incorporated herein by reference).

Labeled protein A or protein G may also be used for this purpose. These proteins are normal constituents of the cell walls of staphylococcal bacteria. They exhibit a strong non-immunogenic reactivity with immunoglobulin constant regions from a variety of species (see, generally Kronral, et al., *J. Immunol.*, 111:1401–1406 (1973), and Akerstrom, et al., *J. Immunol.*, 135:2589–2542 (1985)).

Alternatively, the immunoligand can be directly labeled. A wide variety of labels may be employed, such as radionuclides, fluorescers, enzymes, enzyme substrates, enzyme cofactors, enzyme inhibitors, etc. Numerous types of immunoassays are available and are well known to those skilled in the art (see, e.g., U.S. Pat. Nos. 4,271,140 and 4,098,876).

The ligand component can be conjugated to the immunoglobulin component by a number of methods. For instance, the linkage may be by way of heterobifunctional cross-linkers, such as SPDP, carbodimide, glutaraldehyde or the like. A preferred method is via a peptide bond, by linking DNA segments encoding the ligand and the immunoglobulin constant region.

In one aspect, the present invention is directed to recombinant DNA segments encoding the heavy and light chain constant regions such as human gamma heavy chain regions or human kappa light chain regions. The DNA segments encoding these regions will typically be joined to DNA segments encoding the appropriate ligand, all in accordance with well known procedures.

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, New York, 1989. Other general references are provided throughout this document. The procedures therein are believed to be well known in the art and are provided for the convenience of the reader. All the information contained therein is incorporated herein by reference.

The DNA constructs will typically include an expression control DNA sequence operably linked to the chimeric coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the immunoligands.

It is well known that native forms of "mature" immunoglobulins will vary somewhat in terms of length by deletions, substitutions, insertions or additions of one or more amino acids in the sequences. Thus, both the variable and constant regions are subject to substantial natural modification, yet are "substantially identical" and still capable of retaining their respective activities. Human constant region DNA sequences can be isolated in accordance with well known procedures from a variety of human cells, but preferably immortalized B-cells. Suitable source cells for the DNA sequences and host cells for expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to these naturally-occurring forms of immunoglobulin chains, "substantially identical" modified heavy and light chains can be readily designed and manufactured utilizing various recombinant DNA techniques well known to those skilled in the art. For example, the chains can vary from the naturally-occurring sequence at the primary structure level by several amino acid substitutions, terminal and intermediate additions and deletions, and the like. Alternatively, polypeptide fragments comprising only a portion (usually at least about 60–80%, typically 90–95%) of the primary structure may be produced, which fragments possess one or more immunoglobulin activities (e.g., complement fixation activity), while exhibiting lower immunogenicity. In particular, it is noted that like many genes, the immunoglobulin-related genes contain separate functional regions, each having one or more distinct biological activities. In general, modifications of the genes encoding either the ligand or immunoglobulin component of an immunoligand may be readily accomplished by a variety of well-known techniques, such as site-directed mutagenesis (see, Gillman and Smith, *Gene* 8:81–97 (1979) and Roberts, S. et al., *Nature* 328:731–734 (1987), both of which are incorporated herein by reference).

The nucleic acid sequences of the present invention capable of ultimately expressing the desired immunoligand can be formed from a variety of different polynucleotides (genomic or cDNA, RNA, etc.) by a variety of different techniques. Joining appropriate genomic sequences is presently the most common method of production, but cDNA sequences may also be utilized (see, European Patent Application Nos. 85102655.8, 85305604.2, 84302368.0 and 85115311.4, as well as PCT Application Nos. GB85/00392 and US86/02269, all of which are incorporated herein by reference).

As stated previously, the DNA sequences will be expressed in hosts after the sequences have been operably linked to an expression control sequence (i.e., positioned to ensure the translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In general, prokaryotes are used for cloning the immunoligand DNA sequences. E. coli is one prokaryotic host particularly useful for cloning the DNA sequences of the present invention. Particular E. coli strains that can be used include, HB101, DH-1, and MH-1.

Other microbial hosts suitable for use include bacilli, such as *Bacillus subtilus*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast may also be used for expression. Saccharomyces is a preferred host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

When constructing vectors for use in yeast, the plasmid YRp7 can be used (see, Stinchcomb, et al., *Nature*, 282: 39 (1979)). This plasmid contains the trp1 gene which is a selectable marker for a mutant strain which lacks the ability to grow on media containing tryptophan. The presence of the trp1 gene allows transformed mutant cells to grow on selective media and to be identified.

In addition to microorganisms, mammalian tissue cell culture may also be used to produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, myeloma cell lines, etc, but preferably transformed B-cells or hybridomas. Expression vectors for these cells can include expression control sequences, such as an origin of replication, a promoter, an enhancer (Queen, C. et al., *Immunol. Rev.* 89:49–68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to neomycin, G418, mycophenolic acid and hygromycin.

The vectors can also be constructed to enhance successful molecular packing of the ligand and immunoglobulin components. For instance, the 3' end of the ligand gene can be modified to make the carboxy terminus resemble the hydrophilic—large hydrophobic—hydrophilic—hydrophilic pattern of amino acids commonly observed at the carboxy end of human variable-diversity joining (VDJ) immunoglobulin gene segments (see, Kabat et al., *Sequences of Proteins of Immunological Interest* (1987), which is incorporated herein by reference). This type of alteration will make the carboxy terminus of the ligand similar to the amino acid sequence of several VDJ segments, enhancing favorable structural interactions between the ligand and the Ig constant region.

The vectors containing the DNA segments of interest (e.g., the heavy chain and ligand encoding sequences and expression control sequences) can be transferred into the host cell by well-known methods, depending on the type of cellular host. For example, calcium chloride transfection is commonly utilized for prokaryotic cells, whereas calcium phosphate treatment or electroporation may be used for other cellular hosts. Other methods used to transform mammalian cells include the use of Polybrene, protoplast fusion, liposomes and micro injection (see, generally, Sambrook et al., supra).

Once expressed, the whole immunoligands, their dimers, or individual light and heavy chains of the present invention can be purified according to standard procedures of the art, including ammonium sulfate precipitation, fraction column chromatography, gel electrophoresis and the like (see, generally, Scopes, R., *Protein Purification*, Springer-Verlag, N.Y. (1982)). Once purified, partially or to homogeneity as desired, the polypeptides may then be used therapeutically or in developing and performing assay procedures, immunofluorescent stainings, and the like (see, *generally, Immunological Methods*, Vols. I and II, Eds. Lefkovits and Pernis, Academic Press, New York, N.Y. (1979 and 1981)).

Pharmaceutical compositions comprising immunoligands of the present invention are useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the immunoligand in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 1 mg of immunoligand. A typical composition for intravenous infusion can be made up to contain 250 ml of sterile Ringer's solution, and 1 mg of immunoligand. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference.

The immunoligands of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present immunoligands or a cocktail thereof can be administered for prophylactic and/or therapeutic treatments. In therapeutic application, compositions are administered to a patient already affected by the particular disease, in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg of immunoligand per dose, with dosages of from 1 to 10 mg per patient being more commonly used.

In prophylactic applications, compositions containing the immunoligands or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 100 mg per dose, especially 1 to 10 mg per patient.

Single or multiple administrations of the compositions can be carried out with dose levels and pattern being selected by the treating physician. In any event, the pharmaceutical formulations should provide a quantity of the immunoligands of this invention sufficient to effectively treat the patient.

Kits can also be supplied for use with the subject antibodies in the protection against or detection of a cellular activity or for the presence of a selected cell surface receptor. Thus, the subject composition of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the immunoligand is employed in an assay, this will usually be present in a separate vial. The second antibody is typically conjugated to a label and formulated in an analogous manner with the antibody formulations described above.

The following examples are offered by way of illustration, not by way of limitation.

EXPERIMENTAL

Vector Construction

Figure 1:
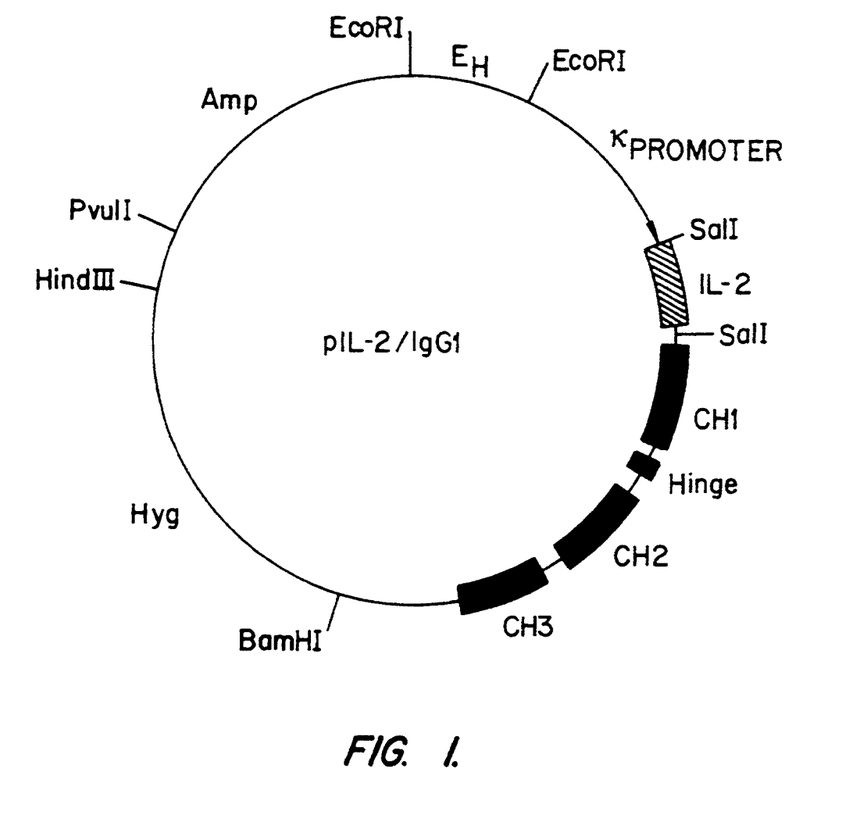

An expression vector (pIL-2/IgG1) that contains the coding sequence of human IL-2 upstream of four exons encoding the human IgG1 heavy chain ($C_H1$, hinge, $C_H2$, $C_H3$) was constructed (FIG. 1).

The pIL-2/IgG1 plasmid was constructed by changing the Xba I site of the vector pVγ1 (Queen, et al. *Proc. Natl. Acad. Sci. USA* 86:10029–10033 (1989) which is incorporated herein by reference) to a Sal I site.

Figure 3:
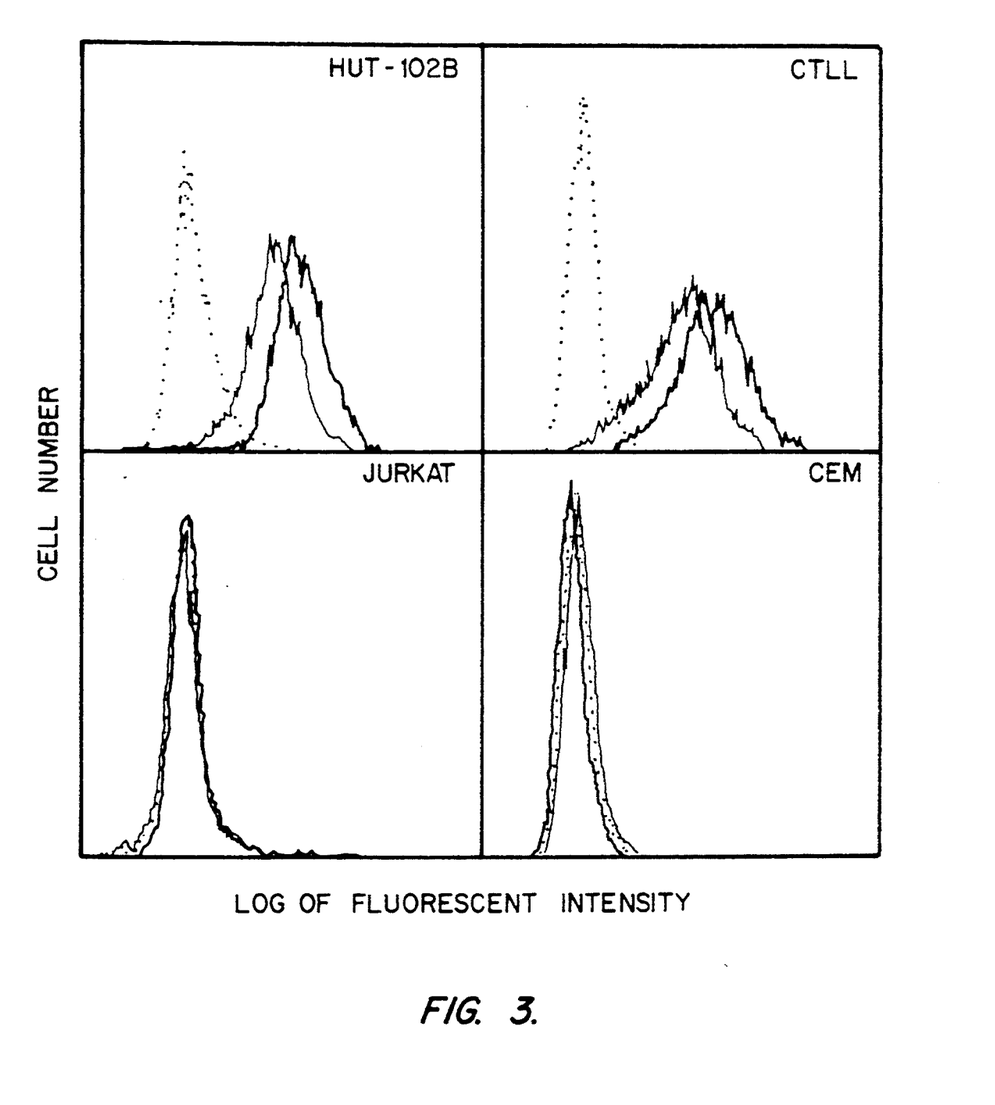

Construction of the pVγ1 plasmid began with the plasmid pKcatH described in the literature (Garcia, J.V. et al., *Nature* 332:383–385 (1986); FIG. 3). This plasmid has the following parts; clockwise:
a. A 700 bp fragment containing the mouse immunoglobulin heavy chain enhancer ($E_H$ in the FIG. 3).
b. An 1100 base pair (bp) fragment from the mouse immunoglobulin light chain kappa gene MOPC 41, containing its promoter. There is a Bgl II site 25 bp after the transcription start site of this promoter.
c. The bacterial CAT gene (800 bp).
d. A splice and polyadenylation signal from the animal virus SV40 (850 bp).
e. Another part of SV40 containing its origin of replication (700 bp);
f. Part of the plasmid pBR322, extending from the Sph I site to the Eco R1 site of the plasmid pML1 (Lusky, M and Botchan, M. *Nature* 293:79–81; 2300 bp) including the Amp gene and origin of replication.

Briefly, pVγ1 was constructed by cutting pKcatH with Bgl II, and then filling in the ends with Klenow polymerase. An Xba I linker, having the sequence GCTCTAGAGC, was inserted at the filled-in Bgl II site. The resulting plasmid was called pKcatH-Xba.

The pKcatH-Xba plasmid was cut partially with Xho II, run on an agarose gel, and full-length linear plasmid (i.e., plasmid cut exactly once with Xho II) was isolated. The DNA was cut with Bam HI, run on a gel and the 5600 bp fragment isolated. Because of its size, this fragment had to extend from the Bam site to the Xho II site at the end of the CAT gene (FIG. 3). The fragment was ligated by itself. The resulting plasmid is called pKcatH-Xba-BX. It is similar to pKcatH but has an Xba I site in place of the Bgl II site and is missing the Xho II-Bam HI SV40 fragment.

Next, pKcatH-Xba-BX was cut partially with Eco RI, run on an agarose gel, and full-length linear plasmid isolated. This DNA was cut with Bam HI, and the 2600 bp fragment isolated. This fragment extended from Eco R1 site before $E_H$ to the Bam HI site. The plasmid pSV2neo (Southern, P.J. and Berg, P. *J. Mol. App. Genet.* 1:327–341 (1982)), was cut with Eco RI and Bam HI, and the large Eco RI-Bam HI fragment ligated to the Eco RI-Bam HI fragment from pKcatH-Xba-BX. The resulting plasmid was called pSV2neo-EH-k.

The pSV2neo-$E_H$-k plasmid was then cut with Xba I and Bam HI and the ends filled in with Klenow polymerase. A 2800 bp fragment containing the human Cγl gene was purified from the phage HG3A (Ellison, J.W. et al., *Nucleic Acids Res.* 10:4071–4079 (1982)), extending from a Hind III site 210 bp before the $C_H1$ exon to a Pvu II site about 1100 bp after the $C_H3$ exon, and the ends filled in. The two fragments were ligated together, and a plasmid selected in which the Hind III site of the second fragment was joined to the Xba I site and the Pvu II site of the second fragment to the Bam HI site. Because of the sequences of these sites, this recreated an Xba I site and a Bam HI site. The new plasmid was called pVγ1neo.

The pVγ1neo plasmid was cut with Hind III and Bam HI, and the large Hind III-Bam HI fragment purified. The plasmid pXBohph containing the Hyg gene (Blochlinger, K. and Diggelmann, H. *Mol. Cell. Biol.* 4:2929–2931 (1984)) was cut with Hind III and Bam HI and a 1600 bp fragment containing the Hyg gene purified. The fragment from pVγ1neo was then ligated to the pXbohph fragment. The resulting plasmid was pVγ1.

The pIL-2/IgG1 plasmid was constructed by changing the Xba I site of pVγ1 to a Sal site. A 503 base pair fragment containing a slightly altered form of the human IL-2 gene (Taniguchi, et al., *Nature* 302:305–310 (1983), which is incorporated herein by reference) was then inserted into the vector. The IL-2 gene differed from the natural human IL-2 sequence in that it encoded an alanine in place of a cysteine at position 125. Also, the 3' end of the IL-2 gene was slightly modified by the addition of a codon for serine, followed by a splice donor site to allow the 3' terminus of IL-2 to be spliced to the 5' end of $C_H1$. A Sal I site was also added to each end of the fragment to facilitate insertion into the vector. The sequence attached to the end of the IL-2 gene was: TCAGGTGAGTCCTTAAAACCTCTCT-CGACCGTCGAC. The serine was added to make the carboxy terminus of IL-2 resemble the hydrophilic-large hydrophobic-hydrophilic-hydrophilic pattern of amino acids commonly observed at the carboxy end of human VDJ segments. A short 235 bp intron separated the modified end of the IL-2 gene from the first of the IgG1 exons, which were in the genomic configuration (FIG. 1).

Transfection

The construct was introduced into the murine non-secreting myeloma cell line Sp2/0 by electroporation. Supernatants from wells containing hygromycin resistent cells were screened for the protein possessing human Ig determinants by an ELISA assay. Approximately 5% of the transfectant supernatants registered positive in the ELISA assay, indicating the secretion of a molecule with human Ig determinants. Transfection into cell lines expressing an endogenous light chain gene did not increase the number of positive supernatants or the level of expression. Subcloning of a positive Sp2/0 transfectant resulted in a cell line (87.20.12) that was more extensively characterized.

Isolation and Characterization of the Immunoligand

The 87.20-12 cell line was incubated with 35-S-methionine; the resulting supernatant was collected and a detergent lysate was prepared from the cells. The lysate was analyzed by immunoprecipitation. To do this, $10^7$ 87.20.12 cells were incubated for 12 hr in 10 ml of DMEM+10% dialyzed fetal calf serum containing 1 mCi $^{35}$S-methionine. Supernatant from labeled cells was concentrated four-fold prior to use; labeled cells were lysed in 0.5% NP-40. Immunoprecipitation was carried out by incubating supernatant or lysate with the indicated antibody-coated agarose for one hour at 4 C with agitation. Immunoprecipitates were analyzed on either a 7.5% or 10% polyacrylamide gel under reducing conditions unless otherwise indicated.

Figure 2A:
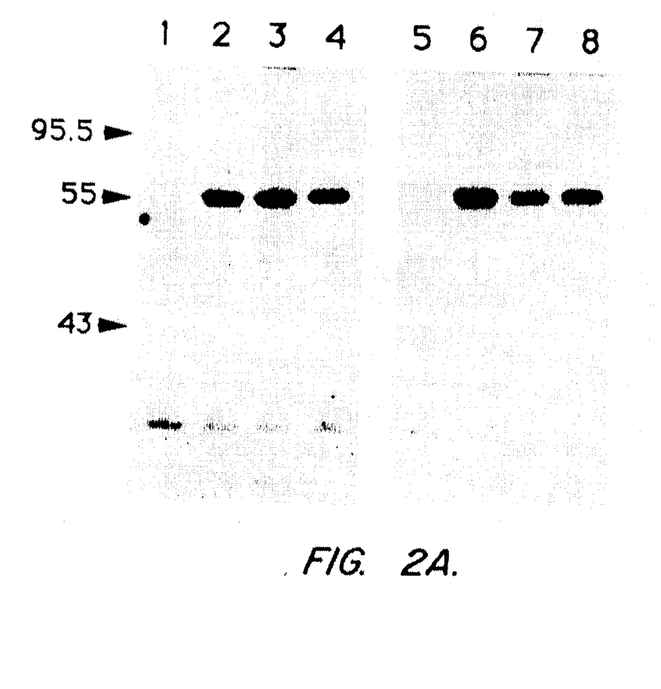
Figure 2B:
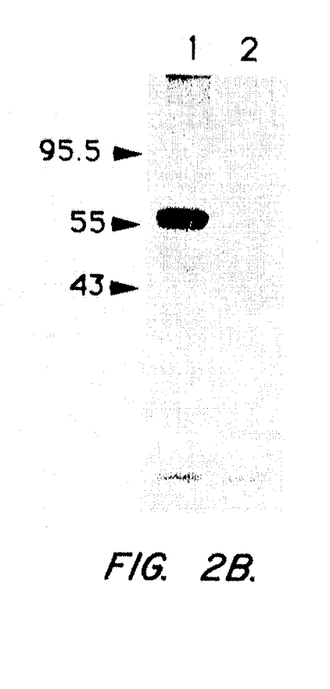
Figure 2C:
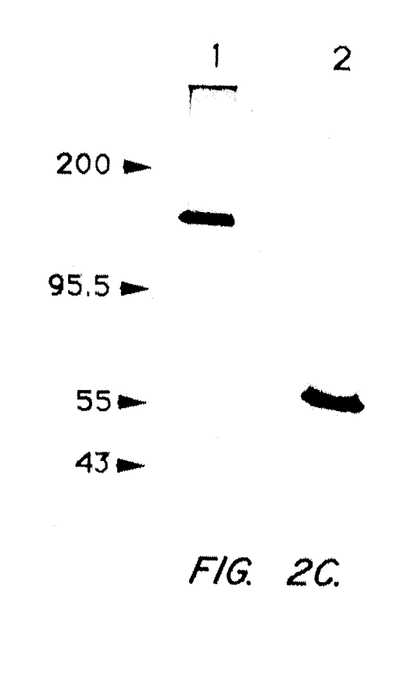

Immunoprecipitation revealed that both the supernatant and the cell lysate contained a molecule of approximately 55 kilodaltons that was specifically precipitated by anti-human IgG coated agarose (FIG. 2a, lanes 2 and 6). A molecule of identical molecular weight was immunoprecipitated by a rabbit anti-human IL-2 antisera (FIG. 2a, lanes 3 and 7) and by protein A coated agarose (FIG. 2a, lanes 4 and 8). No molecules were specifically immunoprecipitated from a labeled lysate of untransfected Sp2/0. Preclearing the 87.20.12 supernatant with anti-human IgG coated agarose removed the molecule reactive with the anti-IL-2 antisera (FIG. 2b), demonstrating that the Ig and IL-2 determinants reside on the same molecule. Thus, the 87.20.12 transfectant secretes a chimeric IL-2/IgG1 molecule.

To establish whether the molecule is secreted as a monomer or in a multimeric form, an immunoprecipitate from a labeled supernatant was electrophoresed under either nonreducing or reducing conditions. The IL-2/IgG1 molecule analyzed under nonreducing conditions displayed approximately twice the molecular weight as that observed under reducing conditions (FIG. 1c), and thus is secreted by 87.20.12 as a homodimer, presumably disulfide linked between the Ig hinge regions.

The chimeric IL-2/IgG gene in pIL-2/IgG1 encodes a 484 residue protein, of which the first twenty amino acids (the natural leader segment of IL-2) should be cleaved prior to secretion (Tanaguchi, supra). Thus, the processed protein (464 amino acids) should have a molecular weight of approximately 51,000 daltons. There is a single asparagine-linked glycosylation site in the $C_H2$ exon of the gene, which occurs naturally in human IgG1 (Hasemann and Capra, *Fundamental Immunology*, Paul (ed.) Raven Press, New York (1989)). Thus, the chimeric gene would be expected to encode a processed, glycosylated molecule of approximately 54,000 daltons. This prediction is in good agreement with that experimentally determined for the molecule secreted by the 87.20.12 transfectant.

To determine whether the IL-2 portion of IL-2/IgG1 is in a native conformation, the ability of the chimeric molecule to bind to cells expressing the IL-2 receptor was assayed by indirect immunofluorescence. FIG. 3 compares the level of fluorescence observed using the chimeric molecule to that obtained using monoclonal antibodies against the p55 chain of the IL-2 receptor. To do this, $2-5 \times 10^5$ cells were incubated for 30 minutes with the indicated reagent at a concentration of 0.5 ug/ml. Cells were washed once prior to incubation with the appropriate FITC-conjugate for 30 minutes at 4. Cells were washed and fixed with 1% paraformaldehyde prior to analysis on a FACScan (Becton-Dickenson).

IL-2/IgG1 binding can be detected to the IL-2 receptor expressing cell lines HuT-102B (human) and CTLL (murine), but not to the IL-2 receptor negative human T cell lines JURKAT and CEM. The level of fluorescence intensity observed on both the human and murine cell line with IL-2/IgG1 is less than that observed with the anti-Tac and PC 61 5.3 monoclonal antibodies, respectively. This is due to the fact that these antibodies recognize the p55 chain of the human and mouse IL-2 receptor, respectively, and thus can detect the excess p55 on the surface of the cell that is not associated with the p75 chain to form the high affinity IL-2 receptor (Waldmann, *Ann. Rev. Biochem.* 58:875–911 (1989)). These results indicate that the IL-2 portion of the chimeric molecule is in a configuration sufficient to allow binding to the IL-2 receptor on the surface of cells. Furthermore, analogous to human IL-2, IL-2/IgG1 demonstrates the ability to bind both human and murine cell surface receptors (Gillis, et al., *J. Immunol.* 120:2027–2032 (1978)).

In order to determine whether the IL-2 portion of the chimeric molecule has complete functional activity, IL-2/IgG1 was purified from 87.20.12 supernatant by passage over a protein A column, and the purified material was analyzed for the ability to support the proliferation of the IL-2/IL-4 dependent murine cell line CTLL (Robb et al., *J. Exp. Med.* 160:1126–1146 (1984)). Stimulation of proliferation of CTLL cells was measured by incubating $5 \times 10^4$ cells for 18 hr with the indicated concentration in a total volume of 200 ul. After an 18 hr incubation, 1 uCi of $^3$H-thymidine was added, and the cells were incubated for an additional 4 hours. Samples were harvested and radioactivity was quantified by scintillation counting.

Figure 4A:
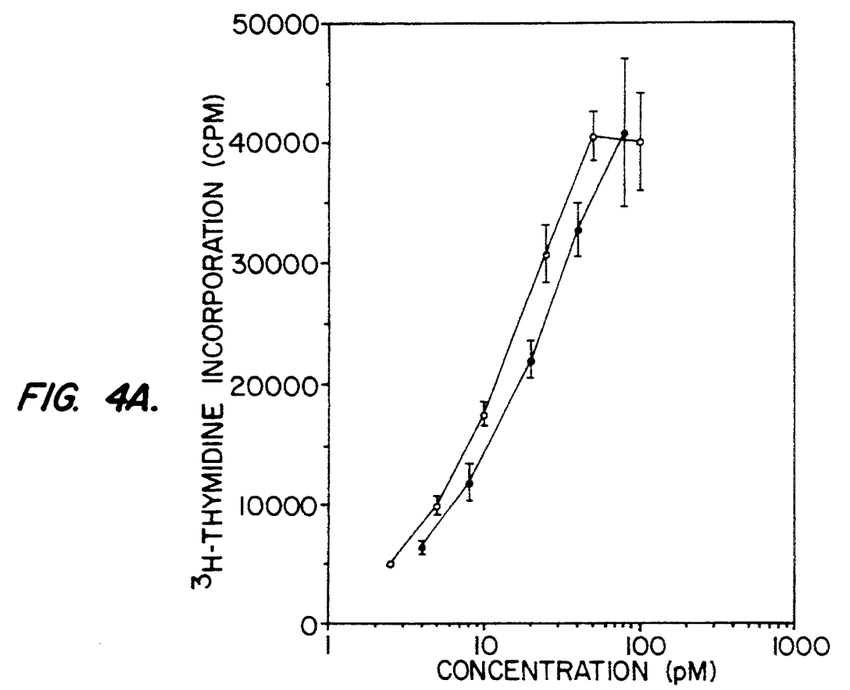

The chimeric molecule was capable of stimulating proliferation of the CTLL cell line, and comparison with the proliferation stimulated by recombinant human IL-2 revealed that on a per molecule basis, the chimeric IL-2/IgG1 has a specific activity indistinguishable from recombinant human IL-2 (FIG. 4a). Thus, the IL-2 moiety of the chimeric molecule is in a fully functional configuration, exhibiting both the binding and proliferation-mediating activities of IL-2.

The functional status of Ig portion of the IL-2/IgG1 molecule was also examined. The capacity for antibody effector function, such as complement fixation and the ability to mediate antibody dependent cell cytotoxicity (ADCC), resides in the Ig constant region. The human IgG1 isotype can mediate both of these effector functions. IL-2/IgG1 was compared with the murine anti-Tac monoclonal antibody for the ability to mediate complement-dependent lysis of the HuT-102B cell line. Complement fixation was carried out by precoating $10^5$ $^{51}$Cr-labeled HuT-102B cells with the indicated concentration of anti-Tac or IL-2/IgG1 for 45 min. at 4 C. The cells were washed twice and adjusted to $5 \times 10^5$/ml. One hundred ul of a 1:2 dilution of rabbit complement was added to 100 ul of cells, and the samples were incubated for 45 min. at 37 C. NP-40 (1%) was substituted for the complement to determine the total radioactive release. Following incubation, one-half of the supernatant was removed to determine $^{51}$Cr release. Specific lysis was calculated as described (Junghans et al., Cancer Res. 50:1495–1502 (1990), which is incorporated herein by reference). All determinations were done in quadruplicate; the standard error of each determination is presented on the graphs.

Figure 4B:
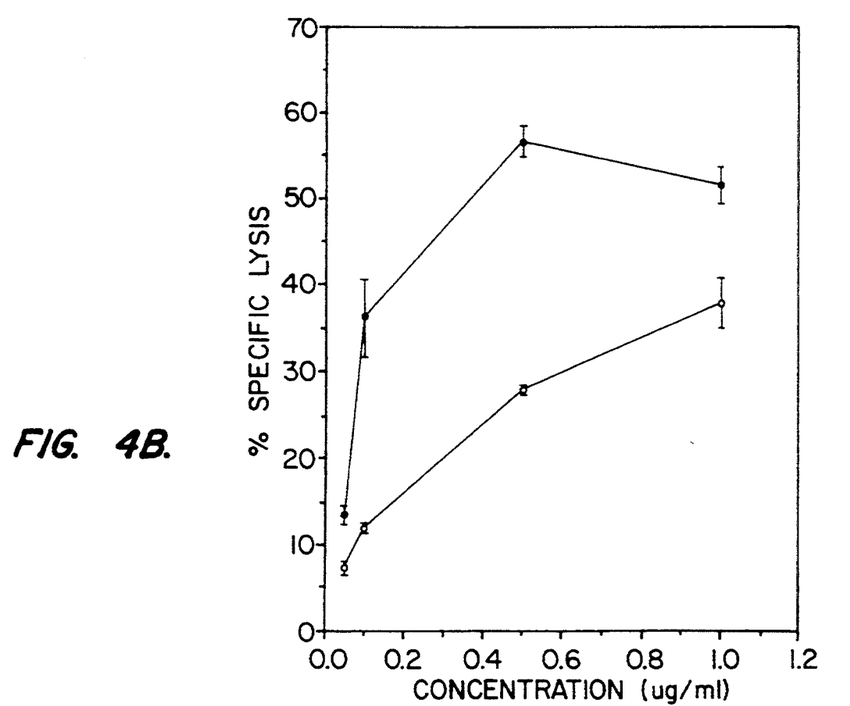

IL-2/IgG1 has the ability to specifically lyse HUT-102B cells in the presence of complement, although at a somewhat less efficient level than does anti-Tac (FIG. 4b). This difference can be attributed to the fact that HuT-102B expresses approximately twenty-fold more anti-Tac binding sites per cell than high affinity IL-2 receptor sites Gillis, et al., supra. IL-2/IgG1 was also examined for the ability to mediate ADCC. The murine anti-Tac monoclonal does not mediate ADCC, however the chimeric and humanized versions of this antibody exhibit detectable levels of ADCC activity with the use of an activated effector cell population (Junghans, et al., Supra. IL-2/IgG1 and chimeric anti-Tac each exhibited a small (28% and 15%, respectively) enhancement of lysis of HuT-102B target cells in a four hour assay. In conclusion, these results indicate that the IL-2/IgG1 molecule possesses the functional activities of both the IgG and IL-2 moieties.

What is claimed is:

1. A chimeric immunoligand comprising:
    an interleukin-2 ligand component comprising an interleukin-2 amino acid sequence capable of binding an interleukin-2 receptor; and
    an immunoglobulin constant region component comprising an immunoglobulin constant region domain without an immunoglobulin variable region domain;
    wherein the ligand component and the constant region component are in peptide linkage, the immunoligand is capable of binding to an interleukin-2 cell surface receptor through the ligand component, and the immunoligand is capable of fixing complement and/or mediating antibody dependent cell cytotoxicity through the constant region component, due to binding of the immunoligand to the cell surface receptor.

2. An immunoligand of claim 1 wherein the constant region component is a heavy chain constant region.

3. An immunoligand of claim 2 wherein the heavy chain is a human IgG1 heavy chain.

4. An immunoligand of claim 2 wherein the constant region component consists of a hinge region, a $C_H2$ domain, and a $C_H3$ domain.

5. An immunoligand of claim 1, wherein the ligand component is linked to the constant region component via a peptide bond to a hinge region of said constant region component.

6. An immunoligand of claim 1 wherein the immunoligand is capable of fixing complement through the constant region component.

7. An immunoligand of claim 1 wherein the immunoligand is capable of mediating antibody dependent cell cytotoxicity through the constant region component.

8. An immunoligand of claim 1 wherein the ligand component is a naturally occurring interleukin-2.

9. An immunoligand of claim 8 wherein the ligand component comprises a human interleukin-2 protein.

10. An immunoligand of claim 8 which is capable of binding an interleukin-2 receptor on a T cell or a B cell.

11. An immunoligand of claim 3, wherein the sequence comprises an additional C-terminal hydrophilic residue.

12. A pharmaceutical composition comprising a suitable carrier and an immunoligand of claim 1, wherein the immunoligand binds to an interleukin-2 receptor.

* * * * *